United States Patent
Gao et al.

(10) Patent No.: US 7,872,746 B2
(45) Date of Patent: Jan. 18, 2011

(54) SINGLE LIGHT SOURCE UNIFORM PARALLEL LIGHT CURTAIN

(75) Inventors: Shawn X. Gao, Irvine, CA (US); David Lloyd Williams, Newport Beach, CA (US); T. Scott Rowe, Dana Point, CA (US); Daryush Agahi, Irvine, CA (US)

(73) Assignee: Alcon, Inc., Hunenberg (CH)

( * ) Notice: Subject to any disclaimer, the term of this patent is extended or adjusted under 35 U.S.C. 154(b) by 467 days.

(21) Appl. No.: 11/955,669

(22) Filed: Dec. 13, 2007
(Under 37 CFR 1.47)

(65) Prior Publication Data

US 2009/0013780 A1 Jan. 15, 2009

Related U.S. Application Data

(60) Provisional application No. 60/871,640, filed on Dec. 22, 2006.

(51) Int. Cl.
*G01N 1/10* (2006.01)
*G01N 23/10* (2006.01)
*G01F 23/292* (2006.01)

(52) U.S. Cl. .................... 356/246; 356/627; 73/293; 378/51

(58) Field of Classification Search ............... 356/244, 356/246, 601, 627; 73/293; 250/577, 575, 250/573; 378/51, 53, 54
See application file for complete search history.

(56) References Cited

U.S. PATENT DOCUMENTS 3,809,891 A * 5/1974 Erdman et al. ........... 250/222.1
3,976,380 A * 8/1976 Rottenkolber et al. ....... 356/458

(Continued)

FOREIGN PATENT DOCUMENTS

DE 1297347 6/1969

(Continued)

OTHER PUBLICATIONS

Peter Weber, Optischer Sensor mibt fullstande in Glasrohen, Feinwerktechnik & Messtechnik, Jan. 1999, pp. 31-33, vol. 99, No. 1/2, Hanser, Munchen, DE.

(Continued)

*Primary Examiner*—Sang Nguyen
(74) *Attorney, Agent, or Firm*—Jonathan E. Prejean

(57) ABSTRACT

A continuous high resolution fluid level monitoring system is provided by embodiments of the present invention. This continuous high resolution fluid level monitoring system includes a unique fluid level sensor having a point light source, parabolic reflector, sensor array, and detection, processing and control system. The point light source illumines a parabolic reflector wherein the point light source is located at the focus of the parabolic reflector. The parabolic reflector reflects light from the point light source to produce a parallel light curtain. This parallel light curtain is parallel to an axis of symmetry of the parabolic reflector. The parallel light curtain illumines a chamber such as a chamber in an ophthalmic surgical device used to contain surgical fluid. The sensor array coupled to the chamber detects the parallel light curtain illuminating the chamber. The sensor array provides an output to a detection/processing/control system in order to determine the fluid level within the chamber. This optical method of determining the surgical fluid levels may be advantageous in that it prevents physical contamination of the surgical fluids.

17 Claims, 4 Drawing Sheets

U.S. PATENT DOCUMENTS

| | | | | |
|---|---|---|---|---|
| 4,009,966 | A | * | 3/1977 | Craig .......................... 356/123 |
| 4,196,961 | A | * | 4/1980 | Walter et al. ............. 359/219.1 |
| 4,274,740 | A | * | 6/1981 | Eidenschink et al. ........ 356/336 |
| 4,286,880 | A | * | 9/1981 | Young ........................ 356/431 |
| 4,395,258 | A | | 7/1983 | Wang et al. |
| 4,402,609 | A | * | 9/1983 | Fetzer et al. ................ 356/640 |
| 4,493,695 | A | | 1/1985 | Cook |
| 4,594,533 | A | * | 6/1986 | Snook et al. ................ 315/363 |
| 4,627,833 | A | | 12/1986 | Cook |
| 4,665,391 | A | * | 5/1987 | Spani ........................ 340/619 |
| 4,713,051 | A | | 12/1987 | Steppe et al. |
| 4,758,238 | A | | 7/1988 | Sundblom et al. |
| 4,775,991 | A | * | 10/1988 | Staudinger et al. ............ 378/51 |
| 4,790,816 | A | | 12/1988 | Sundblom et al. |
| 4,798,580 | A | | 1/1989 | DeMeo et al. |
| 5,008,530 | A | * | 4/1991 | Ball .......................... 250/221 |
| 5,080,457 | A | * | 1/1992 | Fetzer et al. ............. 359/208.1 |
| 5,267,956 | A | | 12/1993 | Beuchat |
| 5,364,342 | A | | 11/1994 | Beuchat et al. |
| 5,424,756 | A | * | 6/1995 | Ho et al. ..................... 345/158 |
| 5,747,824 | A | | 5/1998 | Jung et al. |
| 6,226,081 | B1 | | 5/2001 | Fantone et al. |
| 6,974,948 | B1 | * | 12/2005 | Brent ........................ 250/221 |
| 7,589,340 | B2 | * | 9/2009 | Dancs et al. ................ 250/577 |

FOREIGN PATENT DOCUMENTS

| | | |
|---|---|---|
| DE | 3030259 | 2/1982 |
| EP | 0544945 | 6/1993 |
| EP | 0777111 | 6/1997 |
| WO | WO9920983 | 4/1999 |

OTHER PUBLICATIONS

European Search Report for Application No. 07123297.9, Publication No. 1935383, Published Jun. 25, 2008, 3 pages.

* cited by examiner

SINGLE LIGHT SOURCE UNIFORM PARALLEL LIGHT CURTAIN

CROSS-REFERENCE TO RELATED APPLICATIONS

This application claims priority under 35 U.S.C. §119 to U.S. Provisional Patent Application No. 60/871,640 filed Dec. 22, 2006, the entire contents of which are incorporated herein by reference.

TECHNICAL FIELD OF THE INVENTION

The present invention relates generally to surgical systems and methods. More particularly, the present invention relates to a system and method for sensing a fluid level in a surgical cassette in an ophthalmic surgical system.

BACKGROUND OF THE INVENTION

The human eye in simplest terms functions to provide vision by transmitting light through a clear outer portion called the cornea, and focusing the image by way of a lens onto the retina. The quality of the focused image depends on many factors including the size and shape of the eye, and the transparency of the cornea and lens.

When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL).

In the United States, the majority of cataractous lenses are removed by a surgical technique called phacoemulsification. During this procedure, a thin phacoemulsification cutting tip is inserted into the diseased lens and vibrated ultrasonically. The vibrating cutting tip liquefies or emulsifies the lens so that the lens may be aspirated out of the eye. The diseased lens, once removed, is replaced by an artificial lens.

A typical ultrasonic surgical device suitable for ophthalmic procedures consists of an ultrasonically driven hand piece, an attached cutting tip, an irrigating sleeve, and an electronic control console. The hand piece assembly is attached to the control console by an electric cable and flexible tubing. Through the electric cable, the console varies the power level transmitted by the hand piece to the attached cutting tip and the flexible tubing supply irrigation fluid to, and draw aspiration fluid from, the eye through the hand piece assembly.

In use, the ends of the cutting tip and irrigating sleeve are inserted into a small incision of predetermined width in the cornea, sclera, or other location. The cutting tip is ultrasonically vibrated along its longitudinal axis within the irrigating sleeve by the crystal-driven ultrasonic horn, thereby emulsifying the selected tissue in situ. The hollow bore of the cutting tip communicates with the bore in the horn that in turn communicates with the aspiration line from the hand piece to the console. A reduced pressure or vacuum source in the console draws or aspirates the emulsified tissue from the eye through the open end of the cutting tip, the cutting tip and horn bores, and the aspiration line and into a collection device. The aspiration of emulsified tissue is aided by a saline flushing solution or irrigant that is injected into the surgical site through the small annular gap between the inside surface of the irrigating sleeve and the cutting tip.

Recently, a new cataract removal technique has been developed that involves the injection of hot (approximately 45° C. to 105° C.) water or saline to liquefy or gellate the hard lens nucleus, thereby making it possible to aspirate the liquefied lens from the eye. Aspiration is conducted concurrently with the injection of the heated solution and the injection of a relatively cool solution, thereby quickly cooling and removing the heated solution.

In the liquefracture technique of cataract removal, the cataractous lens is liquefied or emulsified by repetitive pulses of a surgical fluid that are discharged from the hand piece. The liquefied lens may then be aspirated from the eye. Since the surgical fluid is actually used to liquefy the cataractous lens, a consistent, pressurized source of surgical fluid is important to the success of the liquefracture technique. In addition, different surgical fluids may be advantageous for the removal of different hardness of cataracts or for various patient conditions.

Conventional ophthalmic surgical instrument systems use vacuum to aspirate the surgical site and positive pressure to irrigate the site. Typically, a cassette is serially connected between the means used to generate pressure and the surgical instrument. The use of cassettes with surgical instruments to help manage irrigation and aspiration flows at a surgical site is well known. U.S. Pat. Nos. 4,493,695 and 4,627,833 (Cook), U.S. Pat. No. 4,395,258 (Wang, et al.), U.S. Pat. No. 4,713,051 (Steppe, et al.), U.S. Pat. No. 4,798,580 (DeMeo, et al.), U.S. Pat. Nos. 4,758,238, 4,790,816 (Sundblom, et al.), and U.S. Pat. Nos. 5,267,956, 5,364,342 (Beuchat) and U.S. Pat. No. 5,747,824 (Jung, et al.) all disclose ophthalmic surgical cassettes with or without tubes, and they are incorporated in their entirety by this reference. Aspiration fluid flow rate, pump speed, vacuum level, irrigation fluid pressure, and irrigation fluid pressure, and irrigation fluid flow rate are some of the parameters that require precise control during ophthalmic surgery.

For aspiration instruments, the air pressure in the cassette is below atmospheric pressure, and fluid within the cassette has been removed from the surgical site. For irrigation instruments, the air pressure in the cassette is higher than the atmospheric pressure, and the fluid will be transported to the surgical site. In both types of instruments, the cassette acts as a reservoir for the fluid that buffers variations caused by the pressure generation means.

For the cassette to act as an effective reservoir, the level of fluid (and thus the empty volume) within the cassette must be controlled so that the cassette is neither completely filled nor emptied. If fluid fills the cassette in an aspiration system, fluid may be drawn into the means for generating vacuum (typically a venturi), which would unacceptably interfere with the vacuum level of the surgical instrument. An empty cassette in an aspiration system will result in air being pumped into the drain bag, which would waste valuable reservoir space within the bag. Moreover, constant volume within the cassette in an aspiration system enables more precise control level of vacuum within the surgical instrument. Control of the fluid level within cassettes of irrigation systems is similarly desirable.

Additionally, the size of the reservoir within the cassette affect the response time of the cassette. A larger reservoir provides more storage capacity but slows the response time of the system. A smaller reservoir increases the response time of the system, but may not have adequate storage capacity. This dilemma has been addressed by cassettes having two internal reservoirs. Such a cassette is illustrated in U.S. Pat. No. 4,758, 238(Sundblom, et al.) (the "Sundblom Cassette"). The smaller reservoir is in direct fluid communication with the surgical handpiece while a larger reservoir is positioned between the smaller reservoir and the source of vacuum. This allows for a faster response time and larger storage capacity. The small reservoir, however, must be periodically emptied into the larger reservoir prior to the smaller reservoir filling up. This requires that the smaller reservoir contain a fluid level sensor that notifies the control console to empty the smaller reservoir at the appropriate time. The Sundblom Cassette uses two electrical probes 76 (see FIG. 8) that form an open electrical alarm circuit. When the surgical fluid (which is electrically conductive) fills small reservoir 30, both probes 76 are submersed in the fluid, thereby closing the circuit and triggering the alarm that reservoir 30 is full. The fluid level sensor used in the Sundblom cassette has the limitation of being a simple "On/Off" switch. The sensor has no other function other than to trigger a "reservoir full" alarm and provides no other information to the user about the amount of fluid in the small reservoir.

Other pressure sensors, such as the one disclosed in U.S. Pat. No. 5,747,824 (Jung, et al.) use an optical device for continuous fluid level sensing by reading the location of the air/fluid interface. These optical devices require relatively expensive phototransmitters and receivers and are subject to inaccuracies due to foaming of the fluid within the reservoir. In addition, the accuracy of optical pressure sensors can be affected by ambient light levels.

Acoustic pressure sensors have been used in the past to monitor the fluid level in water tanks. The ultrasound transducers are mounted within the tank at the top of the tank and an ultrasound signal is sent downward toward the top of the water contained within the tank. This arrangement, however, is not suitable for use with surgical equipment where sterility is important and the transducer cannot be allowed to come into contact with the fluid. In addition, as surgical devices generally are disposable, locating the transducer within the chamber is undesirable.

Accordingly, a need continues to exist for a simple reliable and accurate fluid level sensor.

SUMMARY OF THE INVENTION

Embodiments of the present invention provide a system and method operable for determining fluid level in an ophthalmic surgical device, and for notifying a user of a liquefracture hand piece of certain fluid level conditions.

More specifically, a continuous high resolution fluid-level monitoring system is provided by embodiments of the present invention. One embodiment of the continuous high resolution fluid level monitoring system includes a unique fluid level sensor having a point light source, parabolic reflector, sensor array, and a detection, processing and control system. The point light source illumines a parabolic reflector wherein the point light source is located at the focus of the parabolic reflector. The parabolic reflector reflects light from the point light source to produce a parallel light curtain. The parallel light curtain is parallel to an axis of symmetry of the parabolic reflector. The parallel light curtain illumines a chamber, such as a chamber in an ophthalmic surgical device, used to contain surgical fluid. The sensor array coupled to the chamber detects the parallel light curtain illuminating the chamber. The sensor array provides an output to a detection/processing/control system in order to determine the fluid level within the chamber. This optical method of determining the surgical fluid levels may be advantageous in that it prevents physical contamination of the surgical fluids.

Yet another embodiment provides a method of determining surgical fluid levels within a chamber of an ophthalmic surgical device.

BRIEF DESCRIPTION OF THE DRAWINGS

For a more complete understanding of the present invention and the advantages thereof, reference is now made to the following description taken in conjunction with the accompanying drawings in which like reference numerals indicate like features and wherein.

DESCRIPTION OF THE INVENTION

Preferred embodiments of the present invention are illustrated in the FIG.'s, like numerals being used to refer to like and corresponding parts of the various drawings.

It is often important to monitor liquid or fluid levels within medical devices. It is important that the fluid levels be monitored and at the same time not be contaminated by the monitoring devices. One such means of doing so is ultrasonic technology. Another way is to use an optical fluid level sensor.

Figure 1:
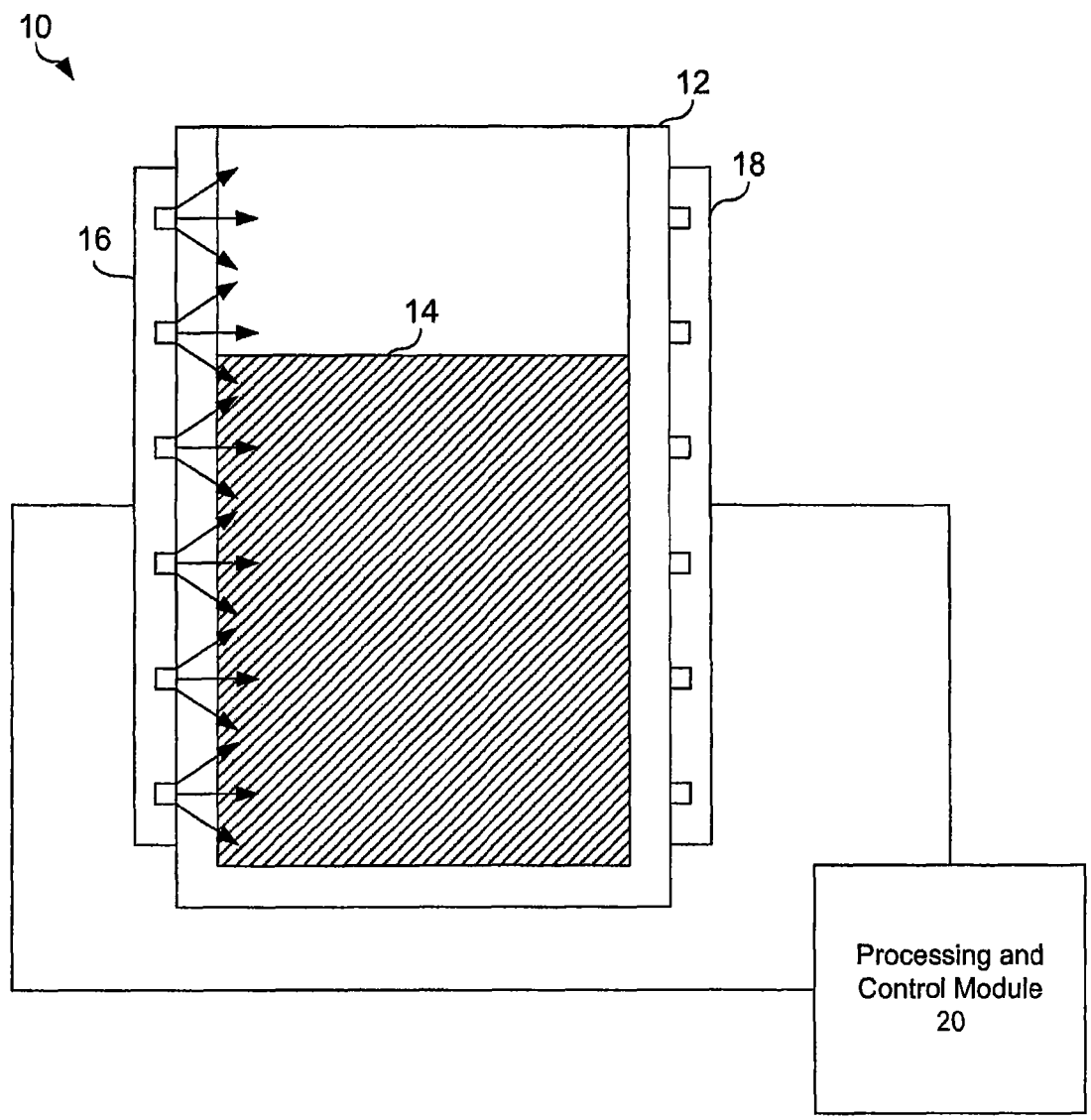
FIG. 1 depicts a prior art solution where a linear light source is used to determine a fluid level within a chamber.

FIG. 1 depicts a prior art solution where a linear light source is used to determine a fluid level within a chamber. Optical level sensing system 10 includes chamber 12, linear light source 16, a linear sensor array 18 and a processing module 20. Linear light source 16 is typically a laser line generator or a linear LED light emitting diode bar. However, these choices for the linear light source typically do not meet the requirements for a continuous high resolution optical level sensing system. This is due to the large viewing angle subtended by the linear light source chosen to illuminate fluid 14 within chamber 12. Additionally, because a number of LED's may be used within linear light source 16, uniformity problems may exist with the intensity of the light generated by the linear light source 16.

In order to achieve uniform intensity the linear light source 16 provided in FIG. 1 typically uses a highly diffused array of LED's. As a result, the light source 16 has a very large viewing angle wherein the rays or beams of light are not parallel. To address this issue, an embodiment of the present invention provides a light curtain wherein the light is substantially uniform and parallel.

Figure 2:
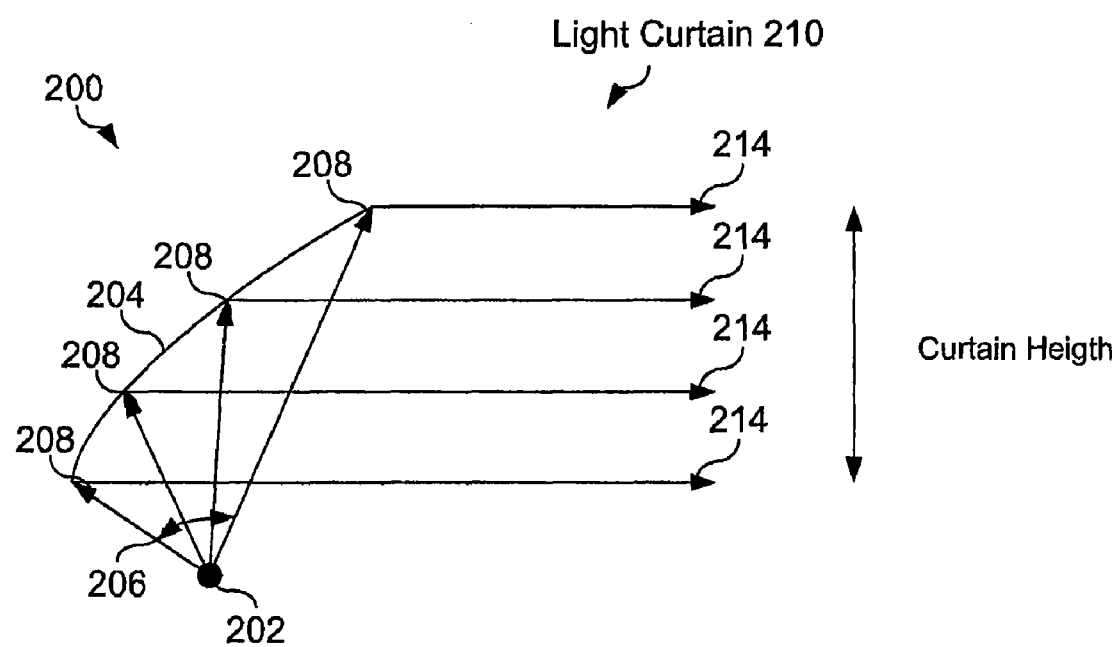
FIG. 2 depicts a linear light source in accordance with an embodiment of the present invention.

FIG. 2 depicts a linear light source 200 used to generate a uniform parallel light curtain in accordance with embodiments of the present invention. This linear light source 200 includes a point light source 202 and a parabolic reflector 204. Point light source 202 is located at the focus of a parabola used to define parabolic reflector 204. Point light source 202 illuminates an arc 206 wherein the rays of light 208 within the arc are not parallel. However, parabolic reflector 204 reflects rays 208 to yield parallel light curtain 210. Parallel light curtain has a curtain 210 height 212. Curtain height 212 may be defined by the requirements of the fluid chamber for which the linear light source 200 may be used to determine the fluid level within. Curtain height 212 may be used to then determine the parabolic arc of the parabolic reflector 204 defined by the parabola. Similarly, once this parabolic arc has been defined, the arc 206 illuminated by the point light source 202 is also defined. The location of the focus of the parabolic reflector 204 again may also be driven by the curtain height 212 requirements associated with the parabolic reflector 204.

The light curtain 210 provided has parallel light rays 214 with a uniform intensity. The uniform intensity results from the illuminating rays originating from a single point light source 202. Additionally, light curtain 210 does not have a large viewing angle because the light rays 214 are in parallel. This is essential to a high-resolution continuous optical level sensing system. The reflector approach offers a smaller size when compared to an optical lens approach, especially when the height of the light curtain 210 is relatively large.

Figure 3:
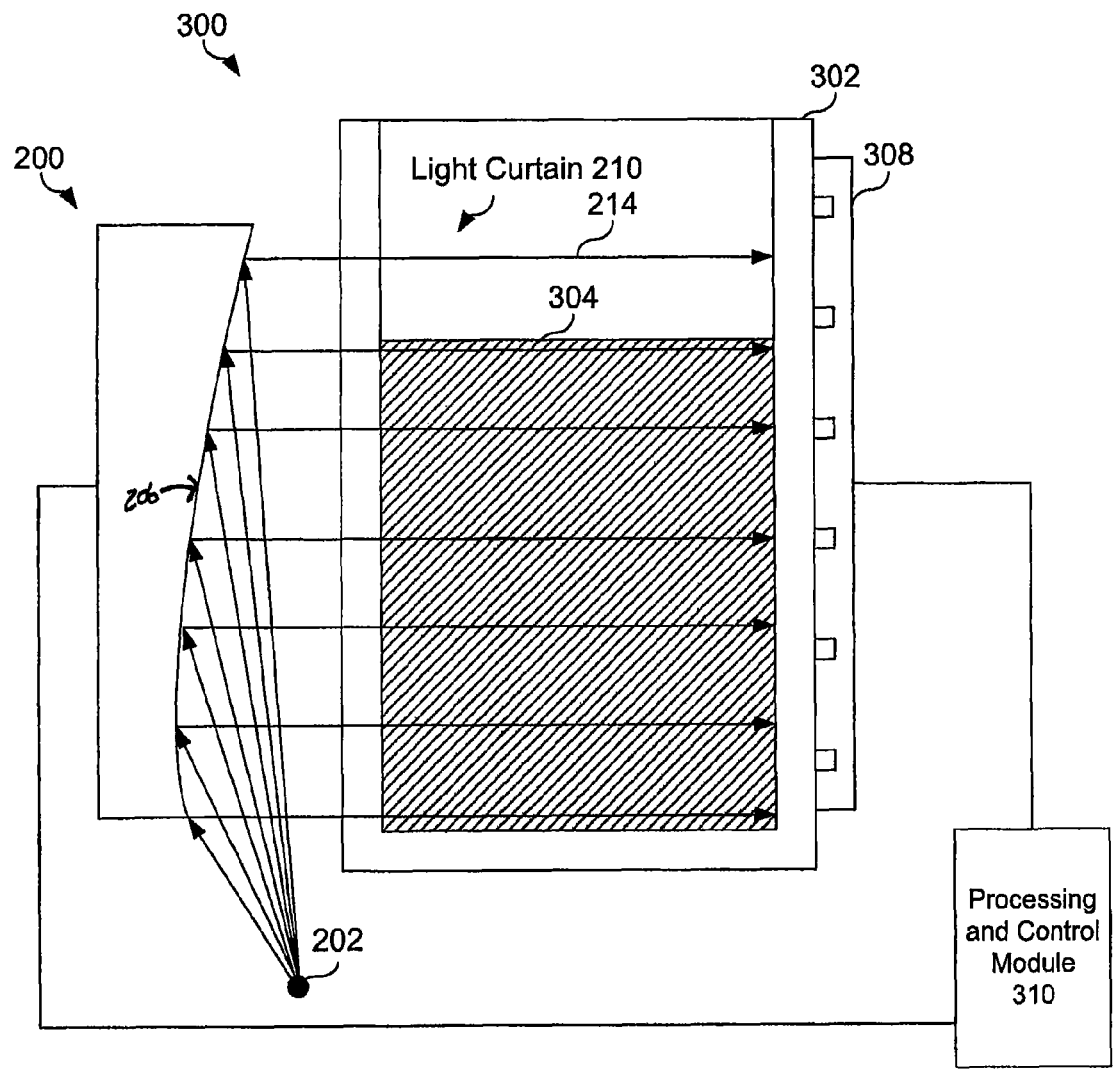
FIG. 3 depicts a fluid-level sensor system in accordance with embodiments of the present invention.

FIG. 3 depicts a fluid-level sensor system 300 in accordance with embodiments of the present invention. Fluid-level sensor System 300 includes a fluid-level sensor using the parabolic linear light source 200 discussed with reference to FIG. 2. Additionally fluid-level sensing System 300 includes a fluid chamber 302 containing fluid 304 and a linear sensor array 308 as well as detection/processing/control module 310. A single-point light source 202 is used to illuminate a parabolic reflector 204 and creates a parallel light curtain 210 having parallels light rays 214. Linear light source 200 may be optically coupled to illuminate fluid chamber 302. The light curtain 210 illuminates the fluid chamber 302 and the light rays from light curtain 210 are detected by sensor array 308. Some of the sensors at sensor array 208 will detect low density light (indicating light that has traveled through fluid 304 and other sensors will detect higher intensity light that has not traveled through fluid 304. Sensor array 308 provides an output to detection/processing/control module 310 representative of the different light intensities received at its sensors. Processing and control module 310 is then able to provide a high resolution continuous measure of the level of the fluid within Chamber 302 based on the signal from sensor array 308 indicating at what height the array detected a substantial change in the intensity of light received, in a manner that will be familiar to those skilled in the art. The fluid level measure (signal) may be used within an ophthalmic surgical device wherein it is important to know when surgical fluid levels are below a certain level, as previously discussed above.

The detection/processing/control module 310 system may be a single processing device or a plurality of processing devices. Such a processing device may be a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on operational instructions stored in memory. The memory may be a single memory device or a plurality of memory devices. Such a memory device may be a read-only memory, random access memory, volatile memory, non-volatile memory, static memory, dynamic memory, flash memory, cache memory, and/or any device that stores digital information. Note that when the system controller implements one or more of its functions via a state machine, analog circuitry, digital circuitry, and/or logic circuitry, the memory storing the corresponding operational instructions may be embedded within, or external to, the circuitry comprising the state machine, analog circuitry, digital circuitry, and/or logic circuitry. The memory stores, and the system controller executes, operational instructions corresponding to at least some of the steps and/or functions illustrated in FIG. 4 associated with embodiments of the present invention.

Figure 4:
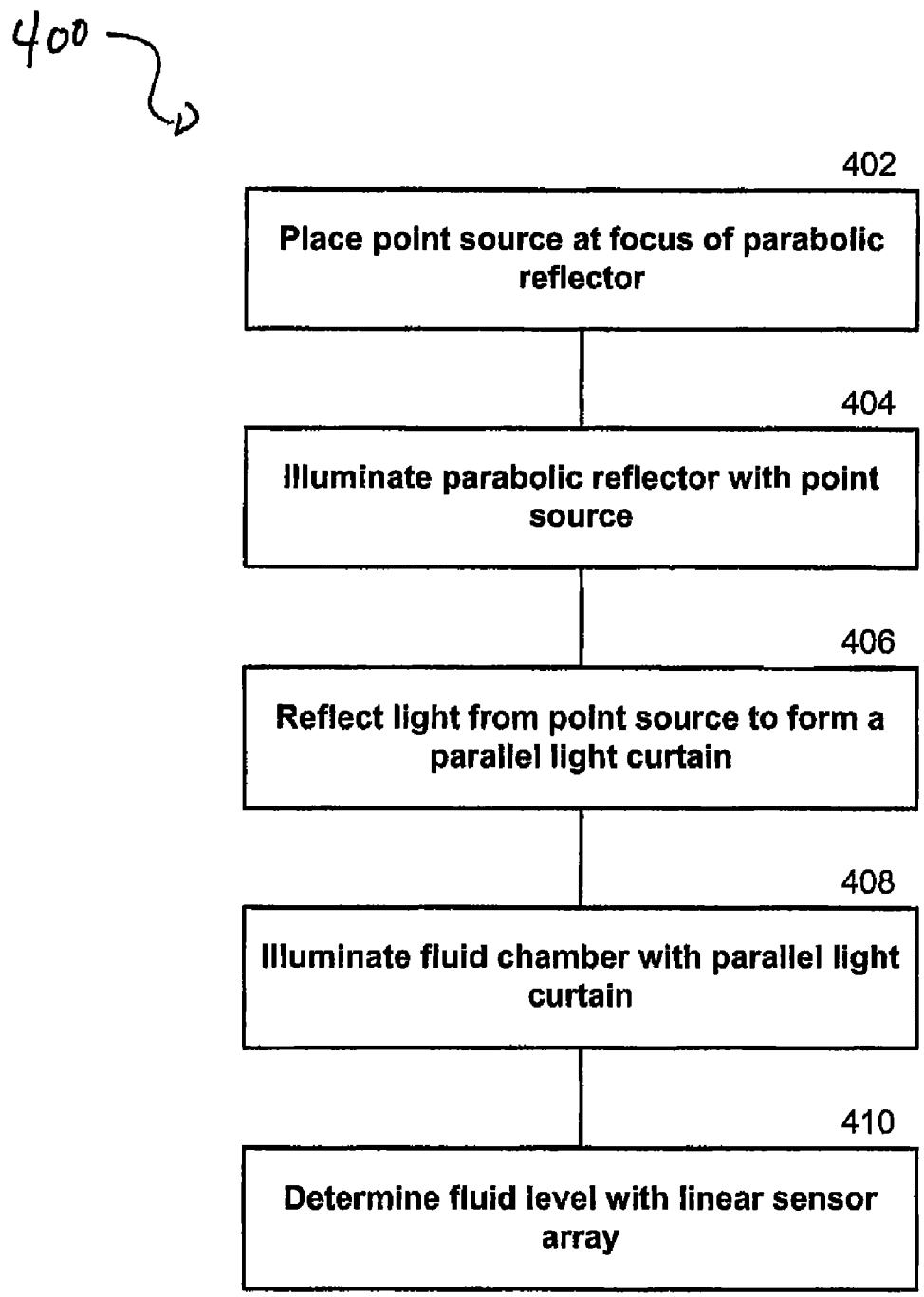
FIG. 4 provides a logic flow diagram of a method of determining the fluid level within a chamber in accordance with embodiments of the present invention.

FIG. 4 provides a logic flow diagram of a method of determining the fluid level within a chamber in accordance with embodiments of the present invention. Operations 400 begin with Step 402 where a point light source is placed at the focus of a parabolic reflector. The parabolic reflector is illuminated by the point light source in Step 404. Light is reflected from the parabolic reflector to produce a parallel light curtain parallel to an axis of symmetry of the parabolic reflector in Step 406. This allows a substantially uniform curtain of parallel light to be generated from a single light source. Additionally the parallel light curtain has a relatively small viewing angle when compared to other light curtains generated using, for example, a linear array of LED's. In Step 408, a fluidic chamber is illuminated, wherein the fluidic chamber may contain a surgical fluid for use within an ophthalmic surgical procedure. A linear sensor array or other sensor array also coupled to the fluidic chamber may then sense/determine a fluid level within the chamber. This allows continuous high resolution determination of the fluid levels within the chamber. The position and height of the parabolic arc may be defined by the required height of the parallel light curtain.

In summary, embodiments of the present invention provide a continuous high resolution fluid level monitoring system and method. Embodiments of the continuous high resolution fluid level monitoring system can include a unique fluid level sensor having a point light source, a parabolic reflector, a sensor array, and a detection, processing and control system. The point light source illumines a parabolic reflector, wherein the point light source is located at the focus of the parabolic reflector. The parabolic reflector reflects light from the point light source to produce a parallel light curtain. The parallel light curtain is parallel to an axis of symmetry of the parabolic reflector. The parallel light curtain illumines a chamber, such as a chamber in an ophthalmic surgical device, used to contain surgical fluid. The ophthalmic surgical device can be, for example, a surgical cassette for use in a phacoemulsification system or vitriol-retinal system as known to those having skill in the art. The sensor array coupled to the chamber detects the parallel light curtain illuminating the chamber. The sensor array provides an output to a detection/processing/control system in order to determine the fluid level within the chamber. This optical method of determining the surgical fluid levels may be advantageous in that it prevents physical contamination of the surgical fluids.

As one of average skill in the art will appreciate, the term "substantially" or "approximately", as may be used herein, provides an industry-accepted tolerance to its corresponding term. Such an industry-accepted tolerance ranges from less than one percent to twenty percent and corresponds to, but is not limited to, component values, integrated circuit process variations, temperature variations, rise and fall times, and/or thermal noise. As one of average skill in the art will further appreciate, the term "operably coupled", as may be used herein, includes direct coupling and indirect coupling via another component, element, circuit, or module where, for indirect coupling, the intervening component, element, circuit, or module does not modify the information of a signal but may adjust its current level, voltage level, and/or power level. As one of average skill in the art will also appreciate, inferred coupling (i.e., where one element is coupled to another element by inference) includes direct and indirect coupling between two elements in the same manner as "operably coupled". As one of average skill in the art will further appreciate, the term "compares favorably", as may be used herein, indicates that a comparison between two or more elements, items, signals, etc., provides a desired relationship. For example, when the desired relationship is that signal 1 has a greater magnitude than signal 2, a favorable comparison may be achieved when the magnitude of signal 1 is greater than that of signal 2 or when the magnitude of signal 2 is less than that of signal 1.

Although the present invention is described in detail, it should be understood that various changes, substitutions and alterations can be made hereto without departing from the spirit and scope of the invention as described.

What is claimed is:

1. A method of determining a fluid level within a chamber, the method comprising:
   placing a point light source at a focus of a parabolic reflector;
   illumining the parabolic reflector with the point light source;
   reflecting light from the parabolic reflector to produce a parallel light curtain continuously extending along a linear sensor array and having light rays parallel to an axis of symmetry of the parabolic reflector;
   illumining a chamber operable to contain a fluid with the parallel light curtain; and
   determining a fluid level within the chamber with the linear sensor array.

2. The method of claim 1, wherein the fluid level is determined continuously by illumining the chamber with the parallel light curtain.

3. The method of claim 1, wherein the parallel light curtain has a substantially uniform intensity.

4. The method of claim 1, wherein the point light source illumines an arc wherein the arc is defined by a height of the parallel light curtain.

5. The method of claim 1, wherein the chamber is within an ophthalmic surgical instrument.

6. The method of claim 1, wherein a focal length and illumination arc of the point light source to the parabolic reflector are determined by a height of the parallel light curtain.

7. A fluid level sensor comprising:
   a point light source;
   a parabolic reflector wherein the point light source is located at a focus of the parabolic reflector, wherein:
      the point light source is operable to illumine the parabolic reflector;
      the parabolic reflector is operable to reflect light from the point light source to produce a parallel light curtain continuously extending along a linear sensor array and having light rays parallel to an axis of symmetry of the parabolic reflector; and
      the parallel light curtain illumines a chamber operable to contain a fluid;
   the linear sensor array being coupled to the chamber, the linear sensor array operable to detect the parallel light curtain illuminating the chamber; and
   a processing system coupled to the sensor array operable to determine the determining a fluid level within the chamber with the linear sensor array.

8. The fluid level sensor of claim 7, wherein the fluid level is determined continuously by illumining the chamber with the parallel light curtain.

9. The fluid level sensor of claim 7, wherein the parallel light curtain has a substantially uniform intensity.

10. The fluid level sensor of claim 7, wherein the point light source illumines an arc wherein the arc is defined by a height of the parallel light curtain.

11. The fluid level sensor of claim 7, wherein the chamber is within an ophthalmic surgical instrument.

12. The fluid level sensor of claim 7, wherein a focal length and illumination arc of the point light source to the parabolic reflector are determined by a height of the parallel light curtain.

13. A fluid level sensor operable to determine a fluid level within a reservoir of an ophthalmic device, the fluid sensor comprising:
   a point light source;
   a parabolic reflector wherein the point light source is located at a focus of the parabolic reflector, wherein:
      the point light source is operable to illumine the parabolic reflector;
      the parabolic reflector is operable to reflect light from the point light source to produce a parallel light curtain continuously extending along a linear sensor array and having light rays parallel to an axis of symmetry of the parabolic reflector; and
      the parallel light curtain illumines a chamber operable to contain a fluid;
   the linear sensor array being coupled to the chamber, the sensor array operable to detect the parallel light curtain illuminating the chamber; and
   a processing system coupled to the linear sensor array operable to determine the determining a fluid level within the chamber with the linear sensor array.

14. The fluid level sensor of claim 13, wherein the fluid level is determined continuously by illumining the chamber with the parallel light curtain.

15. The fluid level sensor of claim 13, wherein the parallel light curtain has a substantially uniform intensity.

16. The fluid level sensor of claim 13, wherein the point light source illumines an arc wherein the arc is defined by a height of the parallel light curtain.

17. The fluid level sensor of claim 13, wherein a focal length and illumination arc of the point light source to the parabolic reflector are determined by a height of the parallel light curtain.

* * * * *